United States Patent [19]
Jensen

[11] Patent Number: 5,951,578
[45] Date of Patent: Sep. 14, 1999

[54] TONGUE CLEANING SYSTEM

[76] Inventor: Charles A. Jensen, 308-709 Houghton Rd, Kelowna, B.C, Canada, VIX7J7

[21] Appl. No.: 09/097,513

[22] Filed: Jun. 15, 1998

[51] Int. Cl.⁶ .............................. A61B 17/24; A61F 9/00
[52] U.S. Cl. ............................................ 606/161; 606/162
[58] Field of Search ...................................... 606/161, 162

[56] References Cited

U.S. PATENT DOCUMENTS

| | | | |
|---|---|---|---|
| 3,809,101 | 5/1974 | Shimizu | 132/76.4 |
| 5,249,389 | 10/1993 | Gallo | 47/1.41 |
| 5,613,262 | 3/1997 | Choy-Maldonado | 606/161 |

*Primary Examiner*—Michael Buiz
*Assistant Examiner*—Vy Q. Bui

[57] ABSTRACT

A tongue cleaning system for cleaning the back of a user's tongue. The system including a tongue holding device and a tongue brush. The tongue holding device is a u-shaped element with textured forwardly disposed inward surfaces. The brush includes a thin head portion with a plurality of bristles of minimal height. The present invention is also described in terms of a method of cleaning one's tongue. The method involves holding one's tongue by way of holding tool, and then brushing the back of the tongue by way of the tongue brush.

1 Claim, 4 Drawing Sheets

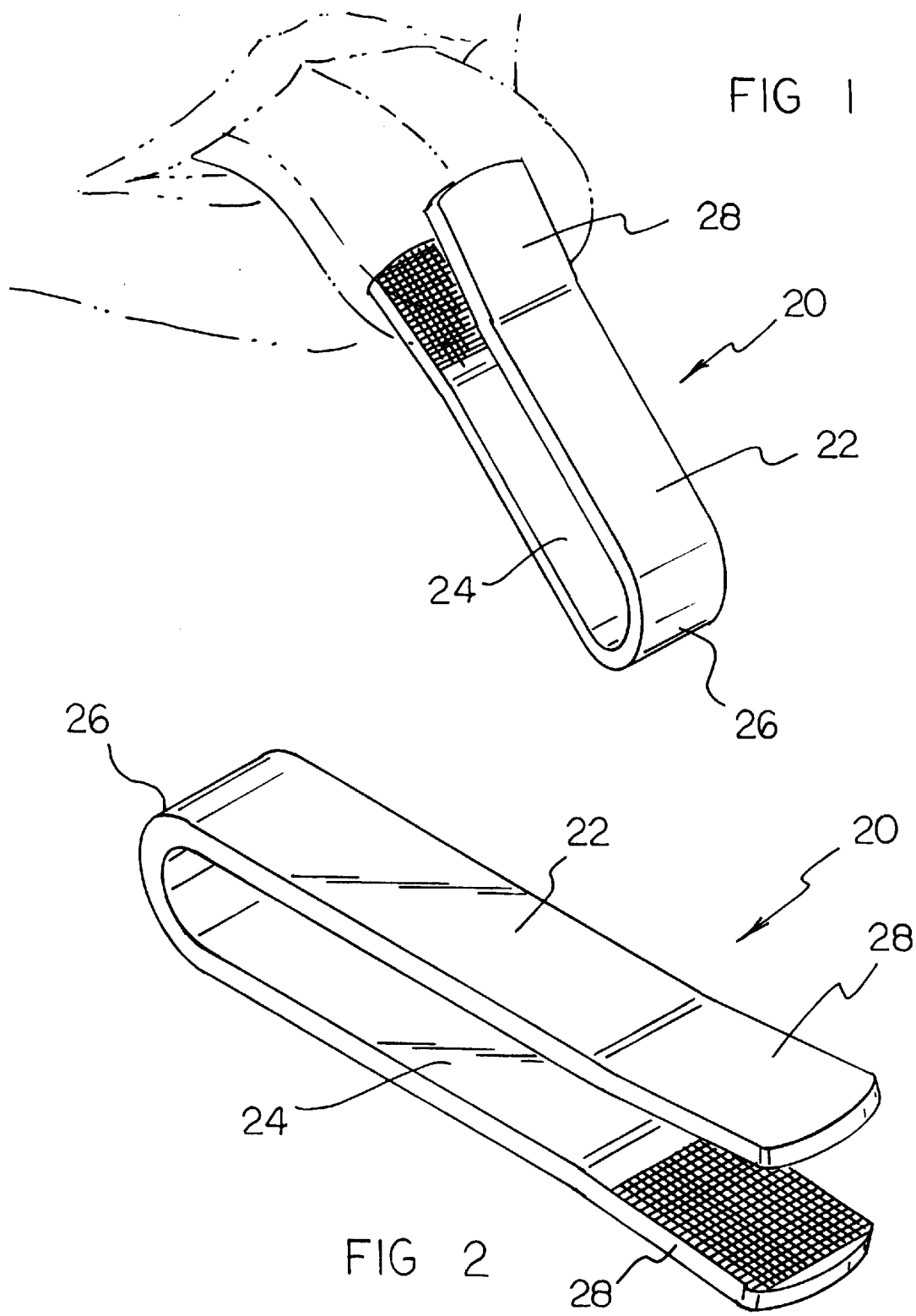

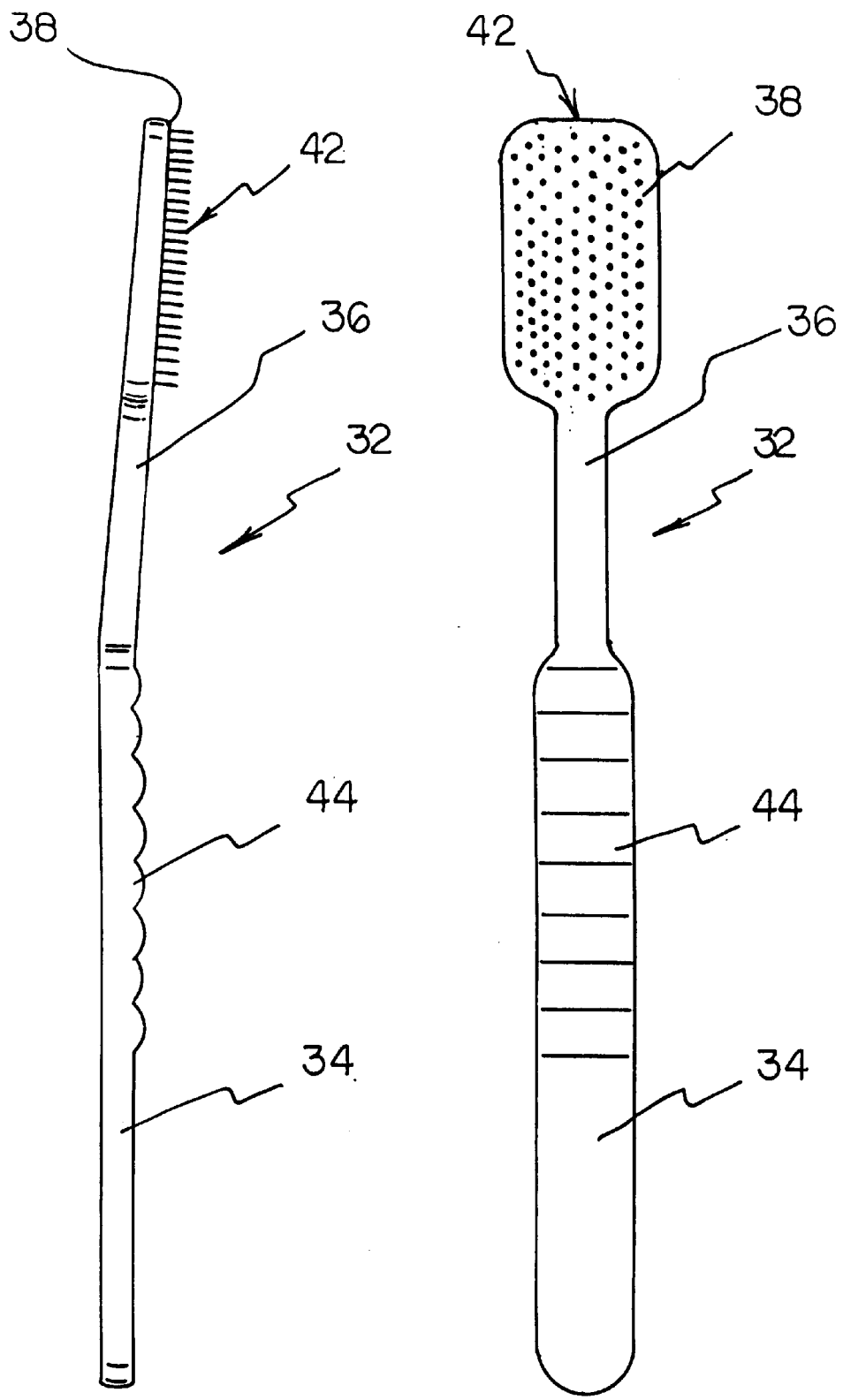

FIG 7
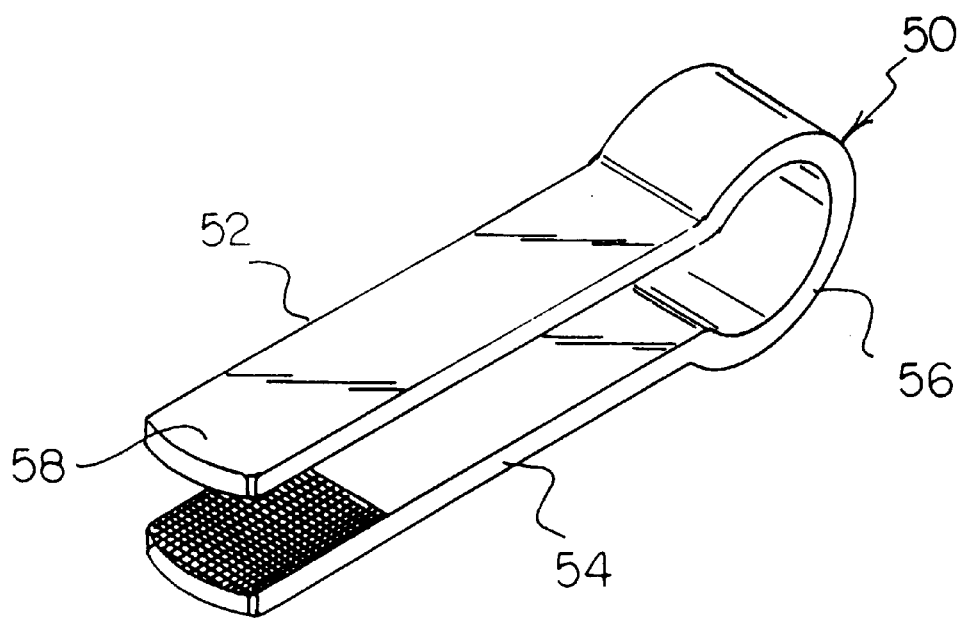
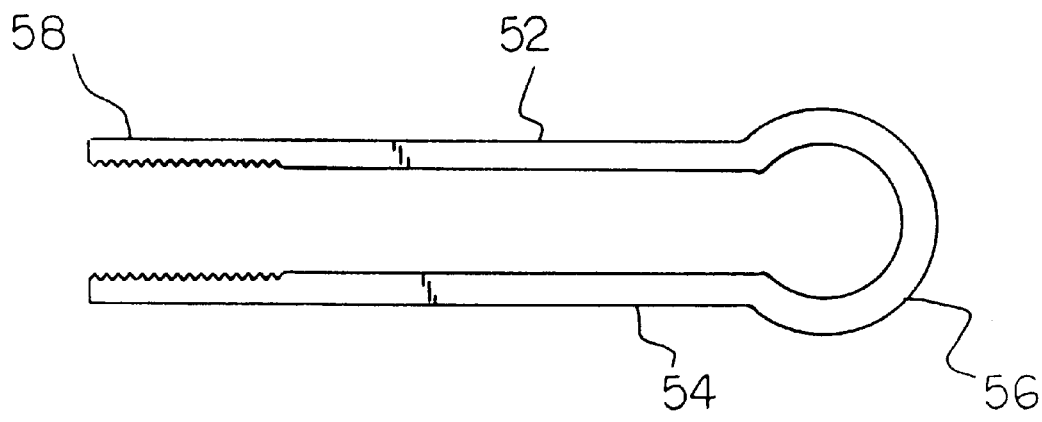
FIG 8

TONGUE CLEANING SYSTEM

BACKGROUND OF THE INVENTION

1. Field of the Invention

The present invention relates to a Tongue cleaning system and more particularly pertains to a system for cleaning the tongue.

2. Description of the Prior Art

The use of tongue cleaning devices are known in the prior art. More specifically, tongue cleaning devices heretofore devised and utilized for the purpose of cleaning the surface of a tongue are known to consist basically of familiar, expected, and obvious structural configurations, notwithstanding the myriad of designs encompassed by the crowded prior art which has been developed for the fulfillment of countless objectives and requirements.

By way of example, U.S. Pat. No. Des. 354,624 to Gupta; U.S. Pat. No. 3,943,592 to Bhaskar et al.; U.S. Pat. No. 5,226,197 to Nack et al.; and U.S. Pat. No. Des. 332,352 to Caldwell et al. all relate to a tongue cleaning device. Furthermore, U.S. Pat. No. 4,754,516 to Tremblay discloses a general brush construction.

While these devices fulfill their respective, particular objectives and requirements, the aforementioned patents do not describe tongue cleaning system that allows the tongue to be held by a tongue holding device while a tongue brush is employed to clean the tongue.

In this respect, the tongue cleaning system according to the present invention substantially departs from the conventional concepts and designs of the prior art, and in doing so provides an apparatus primarily developed for the purpose of a system for cleaning the tongue.

Therefore, it can be appreciated that there exists a continuing need for a new and improved tongue cleaning system which can be used for providing a system for cleaning the tongue. In this regard, the present invention substantially fulfills this need.

SUMMARY OF THE INVENTION

In view of the foregoing disadvantages inherent in the known types of Tongue cleaning devices now present in the prior art, the present invention provides an improved Tongue cleaning system. As such, the general purpose of the present invention, which will be described subsequently in greater detail, is to provide a new and improved Tongue cleaning system and method which has all the advantages of the prior art and none of the disadvantages.

To attain this, the present invention essentially comprises a system for use in cleaning a user's tongue. The system comprises a tongue holding device having an upper leg, a lower leg interconnected with one another at a rounded reward extent. Additionally, each of the legs has a forward extent, with the two forward extents being angularly related away from each other. Each of the forward portions includes a roughened interior surface. This holding device is constructed from a resilient material that will allow the two legs to be urged towards one another. The holding device is adapted to grasp a user's tongue in between the two forward portions. The system also includes a tongue brush which is adapted to be employed in conjunction with the holding device. The brush has a rearward end and a forward end, with the rearward end adapted to be grasped by the user, and the forward end being angularly related with respect to the rearward end. The forward end has essentially planar upper and lower surfaces with a plurality of soft bristles extending from the upper surface of the forward end of the brush. The forward end and bristles together defines a thickness. This thickness is approximately, $5/16$ inches. The rearward end has a plurality of hand engaging ridges for promoting a good grip.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved tongue cleaning system which has all of the advantages of the prior art tongue cleaning devices and none of the disadvantages.

It is another object of the present invention to provide a new and improved tongue cleaning system which may be easily and efficiently manufactured and marketed.

It is further object of the present invention to provide a new and improved tongue cleaning system which is of durable and reliable constructions.

An even further object of the present invention is to provide a new and improved tongue cleaning system which is susceptible of a low cost of manufacture with regard to both materials and labor, and which accordingly is then susceptible of low prices of sale to the consuming public, thereby making such tongue cleaning system economically available to the buying public.

Even still another object of the present invention is to provide a tongue cleaning system for providing a system that will clean the tongue.

Lastly, it is an object of the present invention to provide a new and improved tongue cleaning system for cleaning the back of a user's tongue. The system including a tongue holding device and a tongue brush. The tongue holding device is a u-shaped element with textured forwardly disposed inward surfaces. The brush includes a thin head portion with a plurality of bristles of minimal height. The present invention is also described in terms of a method of cleaning one's tongue. The method involves holding one's tongue by way of holding tool, and then brushing the back of the tongue by way of the tongue brush.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective view of the preferred embodiment of the tongue cleaning system constructed in accordance with the principles of the present invention.

FIG. 2 is a perspective view of the tongue holding device.

FIG. 5 is a side view of the brush in accordance with the present invention.

FIG. 6 is a plan view of the brush in accordance with the present invention.

FIG. 7 is an isometric view of an alternative tongue holding device.

FIG. 8 is a side view of the alternative tongue holding device.

The same reference numerals refer to the same parts through the various Figures.

DESCRIPTION OF THE PREFERRED EMBODIMENT

Figure 4:
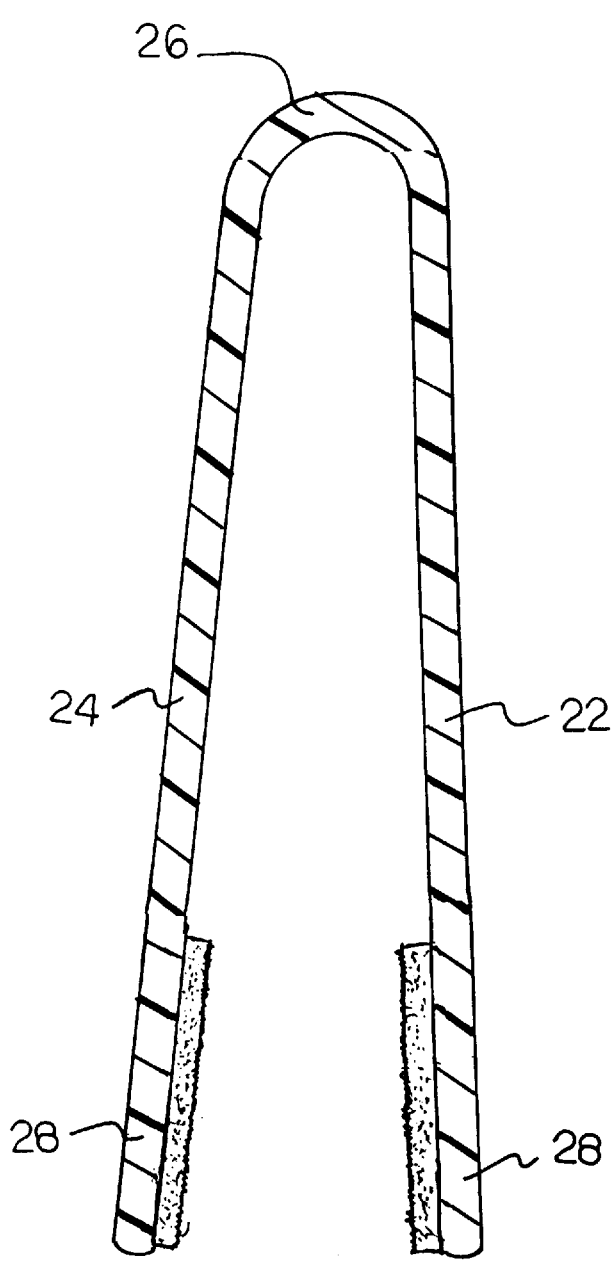
FIG. 4 is a view taken along lines 4—4 of FIG. 3 of the present invention.
Figure 3:
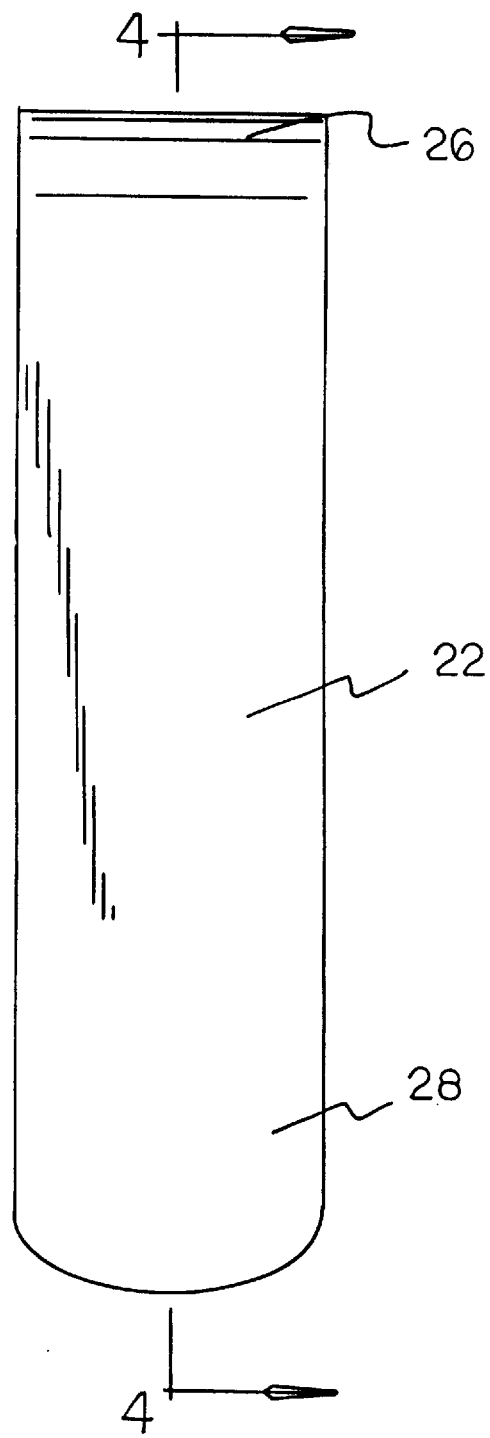
FIG. 3 is a plan view of the tongue holding device of the present invention.

With reference now to the drawings, and in particular to FIG. 1 thereof, the preferred embodiment of the new and improved Tongue cleaning system embodying the principles and concepts of the present invention and generally designated by the reference numeral 10 will be described.

The present invention relates to a system for use in cleaning the back of the user's tongue. The system employs both a tongue holding device and a tongue brush. The tongue holding device is a U-shaped element with textured forwardly disposed inward surfaces. The brush includes a thin head portion with a plurality of bristles of minimal height. The present invention is also described in terms of a method of cleaning one's tongue. The method involves holding one's tongue by way of holding tool, and then brushing the back of the tongue by way of the tongue brush. The various components to both the system and the method will be described in greater detain hereinafter.

Specifically, the present invention includes a tongue holding device 20 constructed from a resilient material such as acrylic. As shown in the Figures, the tongue holding device has an upper leg 22 and a lower leg 24 interconnected with the upper leg by a rounded rearward extent 26 to form a unitary unit. The rounded rearward extent is preferably bulbous in form for reasons that will later become apparent. Further, the tongue holding device has a length of about 3 and ½ inches. The legs are of equal size and shape and have a planar rectangular configuration defined by a pair of parallel, elongated linear side edges and a pair of parallel, short linear end edges. Preferably, the legs and rounded rearward extent each have a constant cross-section along an entire length thereof. Such cross-section preferably has a thickness of about 2 Mil. As shown in FIG. 4, the legs are connected to the rounded rearward extent and angularly related away from each other to define an approximate 10 degree angle.

Each of the forward extents 28 has a gripping mechanism including a square piece of fine grit gripping paper similar to sand paper. Ideally, the gripping paper employs water proof carborundum paper #180. As shown in FIGS. 1 & 2, the gripping paper has a width equal to that of the legs and a length equal to about ⅓ that of the legs. The gripping mechanism further includes a cushioned pad with a periphery having a size and shape equal to that of the gripping paper. A thickness of the cushioned pad is approximately equal to that of the legs. Ideally, the cushioned pad includes double adhesive padded tape.

The holding device is suitably constructed from a resilient material that allows the two legs to be urged towards one another. In use, the holding device serves to grasp a user's tongue in between the two forward extents when pressure is applied.

The present system further includes a tongue brush 32 adapted to be employed in conjunction with the holding device 20. The brush 32 is defined by a reward end 34 and a forward end. The reward end 34, or handle, is adapted to be grasped by the user. The forward end 36 is angularly related with respect to the reward end 34 to enable it to better reach the backside of the tongue. The angular relationship between the forward and rearward ends is best illustrated in FIG. 5.

In the preferred embodiment, the forward end 36 is angled 10 degrees relative to the rearward end 34. The forward end 36 is defined by essentially planar upper and lower surfaces. A plurality of soft bristles 42 extend from the upper surface 38 of the forward end 36 of the brush 32. These bristles 42 are adapted to clean the surface of the user's tongue. The forward end 36 of the brush 32 and associated bristles 42 together define a thickness. This thickness, in the preferred embodiment is approximately 5/16 inches. The forward end 36 of the brush 32 constitutes half of this thickness while the bristles 42 constitute the other half. Additionally, the rearward end 34 of the brush 32 includes a plurality of hand engaging ridges 44, or semi-cylindrical undulations, for promoting a good grip.

An alternative component to the first component of the system is a tongue holding device 50, as shown in FIG. 7. This alternative holding device is defined by an upper leg 52 and a lower leg 54 which are interconnected with one another at a bulbous rearward extent 56. Additionally, each leg of the alternative component is defined by a forward extent 58. The two forward extents 58, of the alternative component, are generally parallel each other. The relationship between the two forward extents 58 can most readily be seen with reference to FIG. 8. Like the first component, each forward extent 58 of the alternative component has a roughened interior surface. The roughened interior surface of the alternative component is for promoting better contact between the legs and the user's tongue. The alternative holding device is constructed from a resilient material. The bulbous rearward extent allows the tongue holding device 50 to grasp onto a tongue having a larger than average diameter, and give the user added control over the holding device.

The steps which make up the method associated with the present invention will not be described. The first step involves providing the above first described tongue holding device or alternative described tongue holding device. The second step involves providing the above described tongue brush. Next, the user's tongue is held in between the forward extents of the upper and lower legs of the holding device. Finally, the back portion of the tongue is brushed by way of the bristles of the tongue brush.

The present invention system for use in cleaning a user's tongue, will allow complete and thorough cleaning of the tongue, for oral hygiene. The invention includes a tongue holding device and a tongue brush. The tongue holding device permits the greatest reach into the back of the mouth. The brush provides gentle firm scrubbing action to the back of the tongue.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by LETTERS PATENT of the United States is as follows:

1. A system for use in cleaning a user's tongue, the system comprising, in combination:

a tongue holding device having an upper leg and a lower leg each with a forward extent and with the lower leg interconnected with the upper leg by a rounded rearward extent in an arcuate configuration in excess of 180 degrees, the legs each having a planar rectangular configuration defined by a pair of parallel, elongated linear side edges and a pair of parallel, short linear end edges, the legs and rounded rearward extent each having a constant cross-section along an entire length thereof, the legs connected to the rounded rearward extent and angularly related away from each other to define an approximate 10 degree angle, each of the forward extents having a gripping mechanism including a square piece of gripping paper having a width equal to that of the legs and a length equal to about ⅓ that of the legs, the gripping mechanism further including a cushioned pad with a periphery having a size and shape equal to that of the gripping paper and a thickness approximately equal to that of the legs, the holding device being constructed from a resilient material that allows the two legs to be urged towards one another, the holding device adapted to grasp a user's tongue in between the two forward extents when pressure is applied; and a tongue brush adapted to be employed in conjunction with the holding device, the brush having a rearward end and a forward end, the rearward end adapted to be grasped by the user, the forward end being angularly related with respect to the rearward end, the forward end being angled ten degrees inward relative to the rearward end, the forward end having an essentially planar upper and lower surface, a plurality of soft bristles extending from the upper surface of the forward end of the brush for cleaning the surface of the user's tongue, the forward end and bristles together defining a thickness, the thickness being approximately 5/16 inches, the forward end of the brush constitutes half of the thickness while the bristles constitutes the other half of the thickness, the rearward end having a plurality of hand engaging ridges for promoting a good grip.

\* \* \* \* \*